United States Patent
Nilawar

(10) Patent No.: US 12,029,752 B2
(45) Date of Patent: Jul. 9, 2024

(54) DIETARY FIBRE COMPOSITION

(71) Applicant: Koye Pharmaceuticals Private Limited, Mumbai (IN)

(72) Inventor: Ajay Nilawar, Mumbai (IN)

(73) Assignee: KOYE PHARMACEUTICALS PRIVATE LIMITED, Mumbai (IN)

( * ) Notice: Subject to any disclaimer, the term of this patent is extended or adjusted under 35 U.S.C. 154(b) by 38 days.

(21) Appl. No.: 16/484,002

(22) PCT Filed: Jul. 6, 2015

(86) PCT No.: PCT/IN2015/000274
§ 371 (c)(1),
(2) Date: Aug. 6, 2019

(87) PCT Pub. No.: WO2016/009443
PCT Pub. Date: Jan. 21, 2016

(65) Prior Publication Data
US 2021/0275568 A1    Sep. 9, 2021

(30) Foreign Application Priority Data

Jul. 4, 2014  (IN) .......................... 2176/MUM/2014

(51) Int. Cl.
| | |
|---|---|
| *A61K 31/718* | (2006.01) |
| *A23L 29/219* | (2016.01) |
| *A23L 29/238* | (2016.01) |
| *A23L 33/00* | (2016.01) |
| *A23L 33/21* | (2016.01) |
| *A61K 31/716* | (2006.01) |
| *A61K 31/721* | (2006.01) |
| *A61K 31/736* | (2006.01) |
| *A61K 45/06* | (2006.01) |
| *A61P 1/00* | (2006.01) |
| *A61P 1/10* | (2006.01) |
| *A61P 3/00* | (2006.01) |
| *A61P 3/06* | (2006.01) |
| *A61P 3/10* | (2006.01) |

(52) U.S. Cl.
CPC .......... *A61K 31/718* (2013.01); *A23L 29/219* (2016.08); *A23L 29/238* (2016.08); *A23L 33/21* (2016.08); *A23L 33/30* (2016.08); *A61K 31/716* (2013.01); *A61K 31/721* (2013.01); *A61K 31/736* (2013.01); *A61K 45/06* (2013.01); *A61P 1/00* (2018.01); *A61P 1/10* (2018.01); *A61P 3/00* (2018.01); *A61P 3/06* (2018.01); *A61P 3/10* (2018.01)

(58) Field of Classification Search
CPC ....... A61K 31/718; A61K 31/736; A61P 1/00; A61P 3/06; A61P 1/10; A61P 3/10; A61P 3/00; C08B 37/0096; C08B 30/12; C08B 30/18; A23L 29/237; A23L 29/219; C08L 3/12; C08L 3/02
See application file for complete search history.

(56) References Cited

U.S. PATENT DOCUMENTS

| | | | | |
|---|---|---|---|---|
| 4,784,861 A | * | 11/1988 | Gori | A23L 33/16 |
| | | | | 426/74 |
| 6,495,190 B1 | * | 12/2002 | Yaginuma | C08L 5/00 |
| | | | | 426/573 |
| 6,630,586 B1 | * | 10/2003 | Fouache | A23K 20/163 |
| | | | | 536/103 |
| 8,617,626 B2 | | 12/2013 | Juergens | |
| 2006/0286260 A1 | * | 12/2006 | Nayak | A23L 29/25 |
| | | | | 426/594 |
| 2017/0156388 A1 | * | 6/2017 | Gallardo | A23L 33/185 |
| 2017/0172196 A1 | * | 6/2017 | Gupta | A23L 33/40 |
| 2017/0224000 A1 | * | 8/2017 | Black | B65D 85/8067 |

FOREIGN PATENT DOCUMENTS

WO    2007035431 A2    3/2007

OTHER PUBLICATIONS

Sanchez-Bayle et al., "The Effect of Fiber Supplementation on Lipid Profile in Children with Hypercholesterolemia" Clinical Pediatrics vol. 40 pp. 291-294 (Year: 2001).*
Reid et al., "Effects of Calcium Supplementation on Serum Lipid Concentrations in Normal Older Women: A Randomized Controlled Trial" Am J Med vol. 112 pp. 343-347 (Year: 2002).*
Marousis et al., "Density and Porosity in Drying Starch Materials" Journal of Food Science vol. 55 No. 5 pp. 1367-1372 (Year: 1990).*
Isleib, D. R., "Density of Potato Starch" American Potato Journal vol. 35 pp. 428-429 (Year: 1958).*
Dengate et al., The Density of Wheat Starch Granules: A Tracer Dilution Procedure for Determining the Density of an Immiscible Dispersed Phase Starch/Starke vol. 30 No. 3 pp. 80-84 (Year: 1978).*
Brown et al., "Cholesterol-lowering effects of dietary fiber: a meta-analysis" American Journal of Clinical Nutrition vol. 69 pp. 30-42 (Year: 1999).*
Turchiuli et al., "Fluidised bed agglomeration: Agglomerates shape and end-use properties" Powder Technology vol. 157 pp. 168-175 doi:10.1016/j.powtec.2005.05.024 (Year: 2005).*
Ohkuma et al., "Fibersol-2: A soluble, non-digestible, starch-derived dietary fibre" Advanced Dietary Fibre Technology, chapter 44 pp. 5090523, published by Blackwell Science Ltd., Oxford, UK. (Year: 2001).*
Dall'Alba et al., "Improvement of the metabolic syndrome profile by soluble fibre—guar gum—in patients with type 2 diabetes: a randomised clinical trial" British Journal of Nutrition vol. 110 pp. 1601-1610 doi:10.1017/S0007114513001025 (Year: 2013).*

(Continued)

*Primary Examiner* — Eric Olson
(74) *Attorney, Agent, or Firm* — ArentFox Schiff LLP

(57) ABSTRACT

A water soluble dietary fibre composition and use thereof is disclosed. The composition comprises: (a) partially hydrolysed and re-polymerized starch, and (b) partially hydrolysed Guar gum.

5 Claims, No Drawings

(56) References Cited

OTHER PUBLICATIONS

Li et al., "NUTRIOSE dietary fiber supplementation improves insulin resistance and determinants of metabolic syndrome in overweight men: a double-blind, randomized, placebo-controlled study" Appl. Physiol. Nutr. Metab. vol. 35 pp. 773-782 doi: 10.1139/H10-074 (Year: 2010).*
C. Lefranc-Millot, "NUTRIOSE® 06: a useful soluble dietary fibre for added nutritional value" Nutrition Bulletin vol. 33 pp. 234-239 (Year: 2008).*
Katada et al., "Partially hydrolyzed guar gum (PHGG) attenuates nonalcoholic steatohepatitis (NASH) in mice through the gut-liver axis" Meeting Info: Digestive Disease Week 2014, Gastroenterology vol. 146 No. 5 suppl 1 p. S-447 abstract Su1467 (Year: 2014).*
Yasukawa et al., "Partially hydrolyzed guar gum affects the expression of genes involved in host defense functions and cholesterol absorption in colonic mucosa of db/db mice" J Clin Biochem Nutr vol. 51 No. 1 pp. 33-38 DOI: 10/3164/jcbn.11-104 (Year: 2012).*
International Search Report dated Feb. 3, 2016, for PCT/IN2015/000274.
International Preliminary Report on Patentability dated Jan. 10, 2017, for PCT/IN2015/000274.

* cited by examiner

DIETARY FIBRE COMPOSITION

RELATED PATENT APPLICATIONS

This application claims the benefit of Indian Patent Application No. 2176/MUM/2014 filed on Jul. 4, 2014, the disclosure of which is incorporated herein by reference in its entirety as if fully rewritten herein. All references including patents, patent applications, and literature cited in the specification are expressly incorporated herein by reference in their entirety.

FIELD OF THE INVENTION

The invention relates to a water soluble dietary fibre composition and its use in treating various health conditions.

BACKGROUND OF THE INVENTION

Dietary fibre is the indigestible component present in food. Recent research suggests that dietary fibre is an essential component in the food, which plays an important role in general well-being. In general, dietary fibre modifies the gastro-intestinal environment and affects how food components are absorbed. Dietary fibre is broadly classified as soluble or insoluble fibres depending on its solubility in water. Typical examples of dietary fibre rich foods include oat bran, whole grains, some fruits, legumes, *psyllium* husk etc. The nature and amount of dietary fibre in the food has shown beneficial effect in various health conditions; mainly those relating to metabolism.

The present innovators have developed a novel water soluble dietary fibre composition, which is organoleptically neutral (tasteless, odourless, and colourless), stable (against moisture, temperature and pH variations) and contains no artificial agents (such as preservatives, colours or other additives).

SUMMARY OF THE INVENTION

Accordingly, there is provided a water soluble dietary fibre composition comprising (a) partially hydrolysed and re-polymerized starch, and (b) partially hydrolysed Guar gum.

In another general aspect, there is provided a method of using the water soluble dietary fibre compositions according to the invention in the treatment of one or more health conditions.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety.

In one general aspect, there is provided a water soluble dietaly fibre composition comprising: (a) partially hydrolysed and re-polymerized starch, and (b) partially hydrolysed Guar gum.

The composition according to the invention comprises a partially hydrolysed and re-polymerized starch. Starch obtained from a wide variety of sources (such as wheat or maize) can be used in the composition according to the invention after it is partially hydrolysed and re-polymerized such that it contains more than 10% cach of the $\alpha$-1,4; $\alpha$-1,6; $\beta$-1,2 and $\beta$-1,3 glycosidic bonds. The extent of hydrolysis and re-polymerization can be controlled to obtain a particular starch grade with a desired proportion of different glycosidic bonds, depending on the intended usc. Commercially available starch which meets the required specifications can also be used, if desired. Typical, non-limiting examples of such commercially available and suitable starch that can be used as such in the composition according to the present invention include NUTRIOSER available from Roquette Frères S.A. (France) 2. In some embodiments, the starch is Dextrin obtained from wheat or maize.

Another key component of the composition according to the invention is a partially hydrolysed Guar gum. Typically, the Guar gum is a high molecular weight polymer with a high viscosity. Generally available guar gum is partially hydrolysed to obtain a comparatively low molecular weight and a low viscosity polymer. The extent of hydrolysis can be controlled to obtain a particular polymeric material with a desired molecular weight and viscosity. Commercially available partially hydrolysed Guar gum which meets the required specifications can also be used, if desired. Typical, non-limiting examples of such commercially available and suitable partially hydrolysed Guar gum that can be used as such in the composition according to the present invention include Sunfiber® available from Taiyo International.

The actual amount of both the components in the composition can vary depending on the specific effect desired and need. In some embodiments, the composition comprises said partially hydrolysed and re-polymerized starch in an amount of about 10 to 90% by weight of the composition. In some embodiments, the composition comprises said partially hydrolysed Guar gum in an amount of about 5 to 40% by weight of the composition.

In some other embodiments, the composition according to the invention comprises (a) partially hydrolysed and re-polymerized starch in an amount of about 80% by weight of the composition, and (b) partially hydrolysed Guar gum in an amount of about 20% by weight of the composition.

The composition has several characteristic properties. For example, the composition is water soluble, organoleptically neutral (tasteless, odourless, and colourless), stable (against moisture, temperature and pH variations) and contains no artificial agents (such as preservatives, colours or other additives).

In some embodiments, the composition according to the invention has a bulk density between 0.2 to 0.6 g/ml.

In some embodiments, the composition according to the invention has untapped bulk density between 0.20 to 0.50 g/ml.

In some other embodiments, the composition according to the invention has tapped bulk density between 0.20 to 0.50 g/ml.

In some embodiments, the composition according to the invention has untapped bulk density between 0.25 to 0.35 g/ml and a tapped bulk density between 0.30 to 0.40 g/ml.

In another general aspect, the composition according to the invention further comprises one or more active or inactive ingredients. The active ingredients provide one or more therapeutic and/or physiological effects. Typical, non-limiting examples, of suitable active ingredients include minerals, vitamins, amino acids, fatty acids, proteins and so on. Suitable examples of active ingredients also include those generally known in the pharmaceutical art. The inactive ingredients do not provide a therapeutic or a physiological effect, but are useful in the formulation of the composition. Typical, non-limiting examples of suitable inactive ingredient include fillers, binders, glidants, lubricants, stabilizers, solubilizers, disintegrants, polymers, sweeteners or flavouring agents.

The compositions according to the invention can be formulated into a wide variety of dosage forms suitable for consumption. Typical, non-limiting examples of such suitable dosage forms include liquid, powder, granules, tablets, pills, capsules, chewable tablets, or gummies.

In some embodiments, the composition is packed as a powder in a sachet.

In another general aspect, there is provided a process for preparing the composition according the invention. In a typical process, the required components are thoroughly mixed together and then packed in the unit packs. The particle size of individual components and the composition as a whole can differ widely depending on the desired properties.

Advantageously, the composition according to the invention can be consumed in a wide variety of ways, as long as it reaches the desired site in required amounts. In some embodiments, the composition in any form is dissolved in water or any other drink and consumed orally. Alternatively, required amount of the composition according to the invention can be mixed in regular food items such as flour, bread, vegetable etc. and then consumed.

The amount of composition that can be consumed by any individual can vary widely depending on the individual (height, weight, age etc.) and the specific effect desired. In some embodiments, the composition according to the invention is consumed in an amount of about 0.1 to 50 gram per day.

The compositions according to the invention are useful in treatment of one or more health conditions. The term "health condition" as used herein refers to and includes disorders and diseases. In general, the health conditions in which the compositions according to the invention can be beneficial include one or more of control of diabetes, weight, cholesterol, blood glucose levels, blood lipid levels, acidity, constipation, mineral absorption, and bowel movement. The present compositions are also useful in promoting general immunity, satiety and absorption of vital food components including minerals and vitamins.

Without limiting to any specific mode of action, it is believed the compositions according to the present invention provide one or more beneficial effects through modification of the gastro-intestinal environment. When a food with low fibre content is consumed, it is digested and absorbed quickly resulting in sharp spikes in blood sugar and lipid levels. However, when a food with higher fibre content is consumed; the fibres in the food interfere with overall digestion and absorption, and thereby result in slow and sustained absorption of various food components, including sugar and lipids.

The fibre available in the compositions also helps in maintaining the overall health of the gastro-intestinal tract.

The compositions according to the invention are also helpful in controlling weight and/or obesity, by controlling the desire to consume food. Typically, compositions according to the invention improve satiety by a combined effect of the following:

(a) reduction in gastric emptying time
(b) reduction in sensitivity to the hunger hormone, Ghrelin, and
(c) increasing sensitivity to various satiety hormones.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Typically, a composition according to the invention was prepared using the following general procedure. Commercially available partially hydrolysed and re-polymerized starch (NUTRIOSE® available from Roquette Freres S.A., France), and partially hydrolysed Guar gum (Sunfiber® available from Taiyo International) were used in this preparation. Both the ingredients were sieved through 40 #separately. For a batch size of 200 kg, three lots each of NUTRIOSE® (53.33 kg) and Sunfiber®. (13.33 kg) were prepared (i.e. 4 parts of NUTRIOSER and 1 part of Sunfiber®). The weighed materials were kept separately.

Step 1

Of the previously weighed materials, 53.33 kg of NUTRIOSE® was charged to a Double Cone Blender, followed by 13.33 kg of Sunfiber®. The contents were mixed for 20 minutes.

Step 2

Second lot of the ingredients (53.33 kg of NUTRIOSE® and 13.33 kg of Sunfiber®) was added to the mixture obtained in Step 1 above, and the contents were mixed for another 20 minutes.

Step 3

Third lot of the ingredients (53.33 kg of NUTRIOSE® and 13.33 kg of Sunfiber®) was added to the mixture obtained in Step 2 above, and the contents were mixed for another 40 minutes. A sample was drawn for analysis at the end of the mixing.

Step 4

The contents from the Step 3 above were removed from the blender and passed through 40 # and dispatched for packing, 5 gm per sachet.

Example 2

The composition was prepared using a procedure outlined in Example 1 and the composition was packaged, 10 gm per sachet.

Example 3

5 gm of product according to Example 1 was administered to 10 individuals having high cholesterol and triglyceride levels for a period of one month. The cholesterol and triglycerides levels were determined again at the end of one month and results are detailed in Table I below. As can be seen, on an average 10-15% reduction in cholesterol levels and about 30-40% reduction in triglyceride levels was observed.

TABLE 1

Effect of dietary fibre composition on cholesterol and triglycerides levels

| | Levels before administration of the dietary fibre composition (mg/dL) | | Levels after administration of 5 gm per day of the dietary fibre composition for one month (mg/dL) | |
|---|---|---|---|---|
| Sr. | Cholesterol | Triglycerides | Cholesterol (5 gm) | Triglycerides (5 gm) |
| 1. | 228 | 219 | 198 | 149 |
| 2. | 210 | 214 | 185 | 150 |
| 3. | 225 | 230 | 190 | 150 |
| 4. | 202 | 212 | 170 | 142 |
| 5. | 205 | 210 | 175 | 135 |
| 6. | 240 | 236 | 198 | 162 |
| 7. | 234 | 224 | 190 | 155 |
| 8. | 212 | 205 | 190 | 132 |
| 9. | 224 | 202 | 194 | 132 |
| 10. | 218 | 208 | 195 | 140 |

The invention claimed is:

1. A method of treating diabetes in humans comprising administering to a subject in need thereof between about 1 and 20 grams per day of a composition comprising:
  (a) partially hydrolysed and re-polymerized starch in an amount of 80% by weight of the composition, and
  (b) partially hydrolysed guar gum in an amount of 20% by weight of the composition,
  wherein (a) and (b) are provided as a mixture of discrete powders in a package prior to administration,
  wherein the composition has a bulk density from about 0.2 g/ml to about 0.6 g/ml, and
  wherein the subject suffers from abnormal blood lipid levels.

2. A method of treating diabetes in humans comprising administering to a subject in need thereof between about 1 and 20 grams per day of a composition comprising:
  (a) partially hydrolysed and re-polymerized starch in an amount of 80% by weight of the composition, and
  (b) partially hydrolysed guar gum in an amount of 20% by weight of the composition,
  wherein (a) and (b) are provided as a mixture of discrete powders in a package prior to administration,
  wherein the composition has a bulk density from about 0.2 g/ml to about 0.6 g/ml
  wherein the subject suffers from one or more of abnormal weight control, abnormal blood glucose levels, acidity, constipation, abnormal mineral absorption, and abnormal bowel movements.

3. The method according to claim 1, comprising administering the composition in an amount of about 5 grams per day.

4. The method according to claim 1, comprising administering the composition in an amount of about 10 grams per day.

5. The method according to claim 1, wherein the abnormal blood lipid levels comprises abnormal cholesterol levels, abnormal triglyceride levels, or a combination thereof.

* * * * *